(12) United States Patent
Zhang

(10) Patent No.: US 8,215,180 B2
(45) Date of Patent: Jul. 10, 2012

(54) APPARATUS FOR TESTING STRENGTH OF OBJECTS

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 358 days.

(21) Appl. No.: 12/551,444

(22) Filed: Aug. 31, 2009

(65) Prior Publication Data

US 2010/0294042 A1    Nov. 25, 2010

(30) Foreign Application Priority Data

May 22, 2009   (CN) .......................... 2009 1 0302542

(51) Int. Cl.
*G01N 9/36*   (2006.01)
(52) U.S. Cl. ............................................ 73/818; 73/760
(58) Field of Classification Search .................... 73/760, 73/818, 831, 855, 856, 865
See application file for complete search history.

(56) References Cited

U.S. PATENT DOCUMENTS

| | | | | |
|---|---|---|---|---|
| 4,702,920 A | * | 10/1987 | Goodman | 425/459 |
| 4,865,094 A | * | 9/1989 | Stroud et al. | 144/176 |
| 5,048,330 A | * | 9/1991 | Link et al. | 73/168 |
| 5,111,701 A | * | 5/1992 | Klein | 73/827 |
| 5,709,518 A | * | 1/1998 | Alexander et al. | 414/401 |
| 5,906,538 A | * | 5/1999 | Welch | 451/241 |
| 6,672,348 B2 | * | 1/2004 | Ransom et al. | 144/287 |
| 7,740,438 B2 | * | 6/2010 | Xiang et al. | 414/256 |

* cited by examiner

*Primary Examiner* — Max Noori
(74) *Attorney, Agent, or Firm* — Altis Law Group, Inc

(57) ABSTRACT

An apparatus for testing strength of a corner portion of an object includes a support platform, an installing mechanism on the platform, a force gauge, a driving mechanism connected to the slidable plate to move the slidable plate, a clamp mechanism for clamping the object in a fixed position, and a push-pull mechanism. The installing mechanism includes two opposite rail plates mounted to the platform, and a slidable plate slidably mounted between the rail plates. The force gauge is fixed to the slidable plate. The push-pull mechanism is connected to the force gauge to be pushed or pulled by the force gauge. The push-pull mechanism comprises two forcing posts to respectively abut against two sides of the object at the corner portion, thereby exerting push or pull force on the two sides of the corner portion to test strength of the corner portion.

9 Claims, 3 Drawing Sheets

APPARATUS FOR TESTING STRENGTH OF OBJECTS

BACKGROUND

1. Technical Field

The disclosure relates to apparatuses for testing strength of objects and, more particularly, to an apparatus for testing strength of molded products.

2. Description of Related Art

Typically, corners of an injection molded product are formed by influx of two or more streams of melted plastic. Because the plastic at the corners cannot bind well, the corners are weak relative to other sections, which can increase risk of damage.

In practice, there is a need to test the strength of injection molded products at the corners. Typically, the sides near the corners of the products are pulled manually to test the strength. However, manual testing is not accurate or efficient.

DETAILED DESCRIPTION

Figure 1:
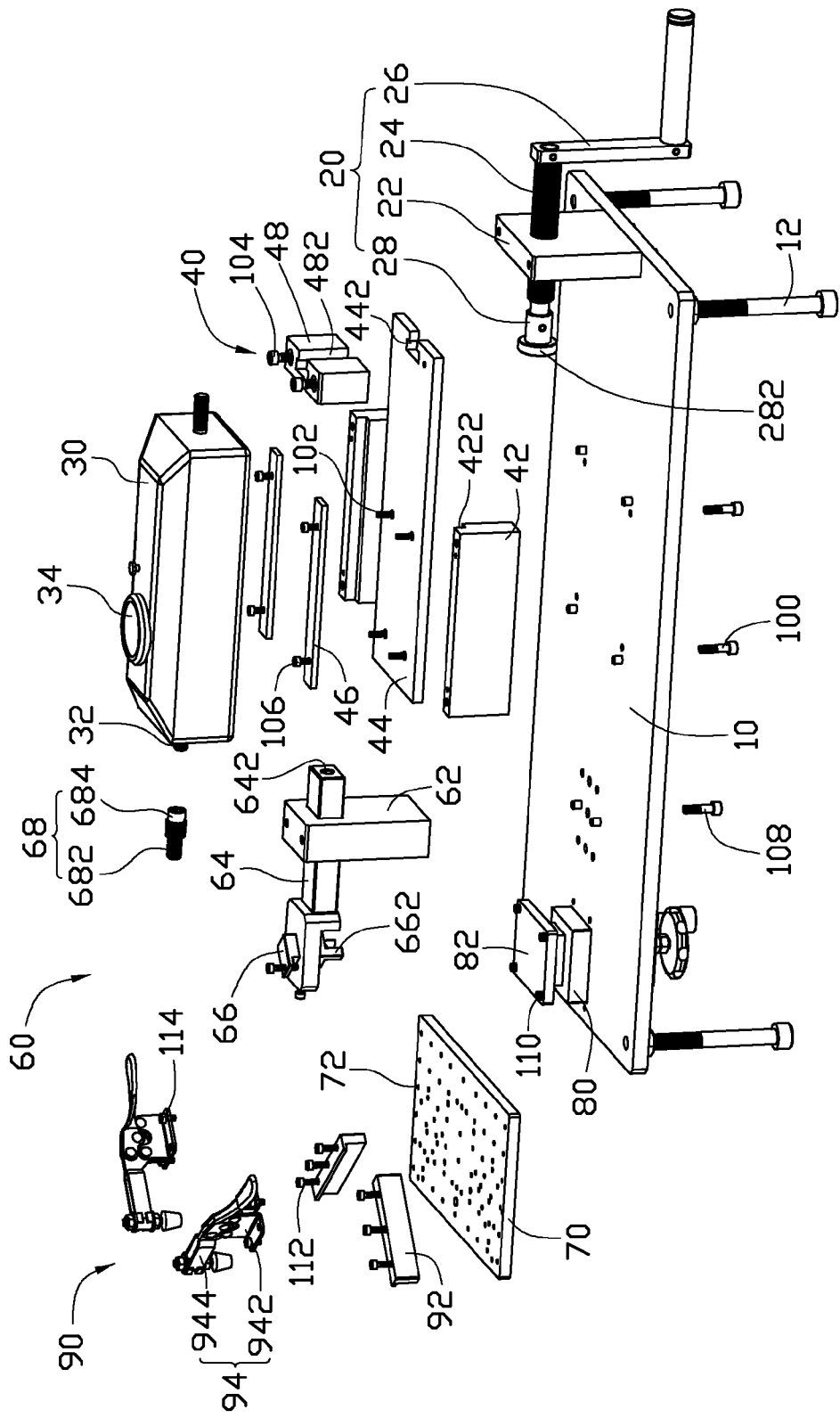
FIG. 1 is an exploded, isometric view showing an exemplary embodiment of an apparatus for testing strength of objects.

Referring to FIG. 1, an exemplary embodiment of an apparatus for testing strength of an object includes a rectangular support platform 10, a plurality of support bolts 12 under the platform 10, a driving mechanism 20, a force gauge 30, an installing mechanism 40 for installation of the force gauge 30 thereon, a push-pull mechanism 60 for exerting push or pull force to the object, an installing board 70 for supporting the object, an adjustment mechanism 80 for adjusting the installing board 70, and a clamping mechanism 90 which can be placed at different positions on the installing board 70.

The driving mechanism 20 includes a support plate 22 extending upright from a first end of the platform 10, a threaded shaft 24 extending through the support plate 22, an L-shaped handle 26 mounted to one end of the threaded shaft 24, and a guiding sleeve 28 secured to the other end of the threaded shaft 24. A flange 282 is formed at the free end of the guiding sleeve 28.

The force gauge 30 includes two threaded screws 32 extending out from two opposite end walls thereof, and a dial 34 on a sidewall thereof.

The installing mechanism 40 includes two rail plates 42 extending oppositely from the platform 10, a slidable plate 44 for mounting the force gauge 30 thereon, two restricting bars 46, and a drive block 48. A sliding rail 422 is defined in each rail plate 42. A T-shaped through slot 442 is defined in one end of the slidable plate 44 corresponding to the flange 282 of the guiding sleeve 28. A T-shaped through slot 482 is defined in the drive block 48 corresponding to the through slot 442.

The push-pull mechanism 60 includes a stand portion 62, a sliding portion 64 slidably extending through the stand portion 62, a driving portion 66 adjustably mounted to one end of the sliding portion 64, and a connecting portion 68. A screw hole 642 is defined in the other end of the sliding portion 64. Two forcing posts 662 are formed at the bottom side of the driving portion 66. The connecting portion 68 includes a threaded post 682 at one end corresponding to the screw hole 642, and a threaded sleeve 684 at the other end corresponding to one threaded screw 32 of the force gauge 30.

Figure 2:
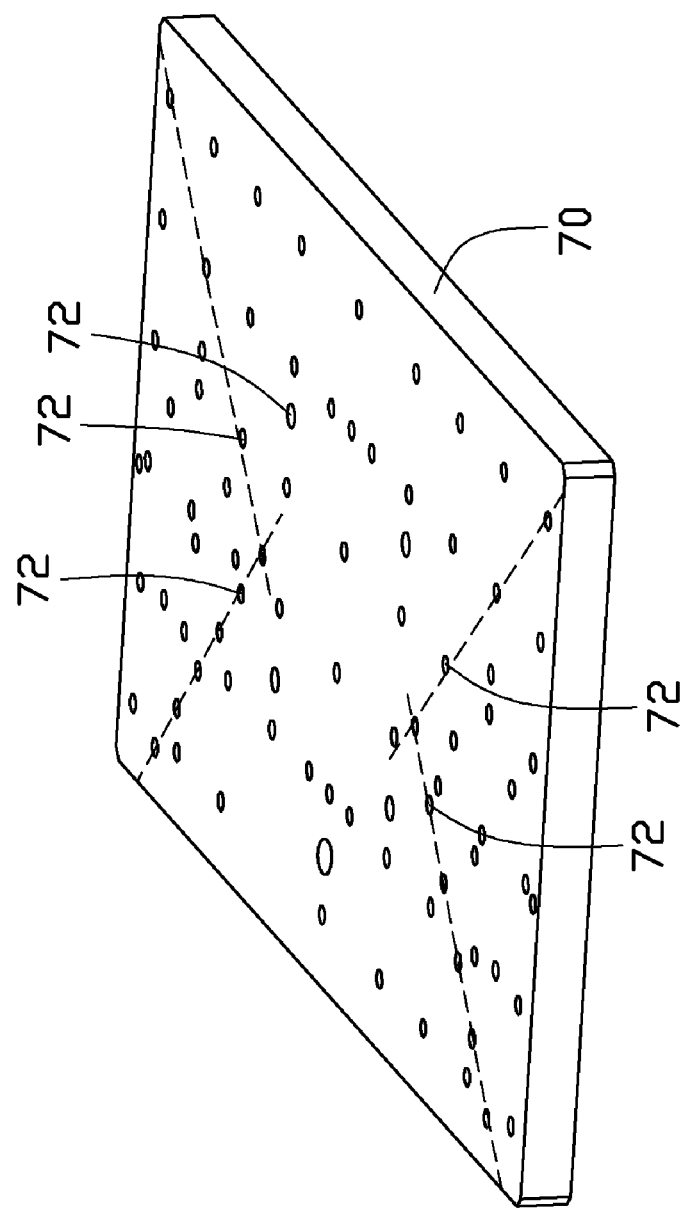
FIG. 2 is an enlarged view of an installing board of the apparatus of FIG. 1.

Referring also to FIG. 2, the installing board 70 defines a plurality of screw holes 72 therein. Some of the screw holes 72 are linearly arranged as shown in FIG. 2 along the dashed lines.

The adjustment mechanism 80 is attached on a second end of the platform 10 opposite to the first end thereof, and includes a pedestal 82 vertically movable relative to the platform 10.

The clamping mechanism 90 includes two blocking portions 92 and two clamps 94. Each clamp 94 includes a fixing bracket 942 and a clamping portion 944 pivotably attached to the fixing bracket 942.

Figure 3:
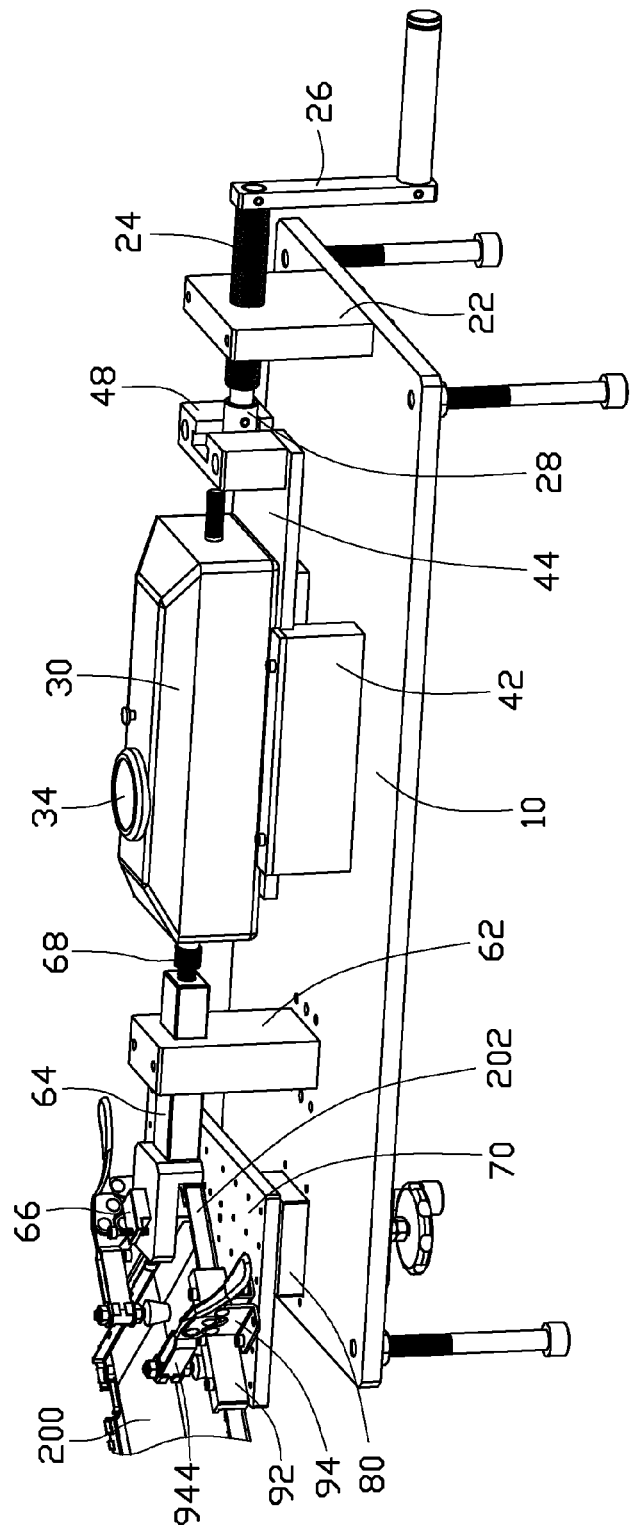
FIG. 3 is an assembled view of the apparatus of FIG. 1, in testing an object.

Referring also to FIG. 3, in assembly, the rail plates 42 of the installing mechanism 40 are mounted to the platform 10 using screws 100. The force gauge 30 is mounted to the slidable plate 44 using screws 102, and the drive block 48 is mounted to the slidable plate 44 using screws 104. The through slot 482 of the drive block 48 aligns with the through slot 442 of the slidable plate 44. The slidable plate 44 is placed between the two rail plates 42 and positioned on the sliding rails 422. The flange 282 of the guiding sleeve 28 of the driving mechanism 20 extends through the through slot 442 and enters the through slot 482. The restricting bars 46 are mounted to the tops of the rail plates 42 using screws 106, to restrict two opposite sides of the slidable plate 44. Thus, the slidable plate 44 is slidably mounted between the rail plates 42.

The threaded post 682 of the connecting portion 68 is screwed into the screw hole 642 of the sliding portion 64 of the push-pull mechanism 60. The stand portion 62 is mounted to the platform 10 using screws 108, and positioned between the force gauge 30 and the adjustment mechanism 80. The connecting portion 68 is rotated to partly screw out the threaded post 682 to make the threaded sleeve 684 engage with the threaded screw 32 of the force gauge 30. Thus, the force gauge 30 is connected to the sliding portion 64. The installing board 70 is fixed onto the pedestal 82 of the adjustment mechanism 80 using screws 110. The blocking portions 92 and the fixing bracket 942 of the clamps 94 are mounted on different positions of the installing board 70 using screws 112, 114 according to need.

Referring to FIG. 3, the object to be tested is an injection molded product 200, which has a right-angle corner portion 202. The blocking portions 92 are mounted on the installing board 70 and arranged at an angle of 90 degrees to each other. The fixing bracket 942 of the clamps 94 are mounted on the installing board 70 and located outside of the corresponding blocking portions 92. The product 200 is placed inside of the blocking portions 92 with two adjacent sides at the corner portion 202 abutting against the blocking portions 92. The clamping portion 944 of each clamp 94 clamps the product 200 onto the installing board 70. The pedestal 82 of the adjustment mechanism 80 is moved upward until the forcing posts 662 abut against inner surfaces of the two adjacent sides at the corner portion 202. The handle 26 is rotated to drive the threaded shaft 24 to rotate relative to the support plate 22 and move in a direction away from the product 200. The slidable plate 44 is moved together with the threaded shaft 24 via the guiding sleeve 28 and the drive block 48. The force gauge 30 pulls the sliding portion 64 via the connecting portion 68. Therefore, the forcing posts 662 exert pulling force on the inner surfaces of the two adjacent sides at the corner portion 202, causing the two adjacent sides to be deformed in different directions. When the reading on the dial 34 of the force gauge 30 is equal to or greater than a predetermined value, then rotation of the handle 26 is stopped. In this circumstance, if the corner portion 202 does not break or come apart, the product 200 passes the strength testing; if the corner portion 202 breaks or comes apart, the product 200 does not pass. Thus, testing efficiency is improved and testing is less labor intensive.

In other embodiments, the installing board 70 and the adjustment mechanism 80 can be omitted if the screw holes 72 is defined in the platform 10 and the blocking portions 92 and the clamps 94 are directly mounted onto the platform 10. In other testing, the apparatus can exert pushing force on the product 200 by rotation of the handle 26 in the reverse direction.

To remove the force gauge 30, first, remove the restricting bars 46. The connecting portion 68 is rotated to disengage the threaded sleeve 684 from the threaded screw 32. Take up the slidable plate 44, to make the flange 282 of the guiding sleeve 28 leave the T-shaped through slot 482 of the drive block 48 and the T-shaped through slot 442 of the slidable plate 44. Thus, the force gauge 30 is easily removed.

It is to be understood, however, that even though numerous characteristics and advantages of the disclosure have been set forth in the foregoing description, together with details of the structure and function of the disclosure, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. An apparatus for testing strength of an object, the apparatus comprising:
    a support platform;
    an installing mechanism comprising two opposite rail plates mounted to the platform, and a slidable plate slidably mounted between the rail plates;
    a force gauge fixed to the slidable plate;
    a clamp mechanism for clamping the object;
    a driving mechanism connected to the slidable plate to move the slidable plate and the force gauge; and
    a push-pull mechanism connected to the force gauge to be pushed or pulled by the force gauge and exerting push or pull force on the object;
    wherein the installing mechanism further comprises a drive block mounted to one end of the slidable plate which is adjacent to the driving mechanism; the driving mechanism comprises a support plate secured to the platform, a threaded shaft screwed through the support plate, an operating handle at one end of the threaded shaft, and a guiding sleeve mounted to the other end of the threaded shaft, the guiding sleeve is connected to the drive block; and
    wherein the drive block defines a T-shaped through slot, a flange is formed at a free end of the guiding sleeve to be received in the through slot of the drive block.

2. The apparatus of claim 1, wherein the slidable plate defines a T-shaped through slot in alignment with the through slot of the drive block for entry of the flange of the guiding sleeve.

3. The apparatus of claim 1, wherein the rail plates each define a sliding rail in an inner side thereof, two opposite sides of the slidable plate are slidable along the sliding rails; the installing mechanism further comprises two restricting bars mounted to top portions of the rail plates to restrict the opposite sides of the slidable plate.

4. The apparatus of claim 1, further comprising an adjustment mechanism mounted to the platform, and an installing board mounted to the adjustment mechanism and vertically movable relative to the platform, the clamping mechanism is attached to the installing board.

5. The apparatus of claim 4, wherein the clamping mechanism includes two blocking portions and two clamps selectively attached on different positions of the installing board.

6. The apparatus of claim 5, wherein each of the clamps comprises a fixing bracket mounted to the installing board, and a clamping portion pivotably attached to the fixing bracket.

7. The apparatus of claim 6, wherein the installing board defines a plurality of screw holes therein, at least part of the screw holes are linearly arranged; the fixing brackets and the blocking portions are fixed on different positions of the installing board via screws being engaged in different screw holes.

8. The apparatus of claim 1, further comprising a plurality of support bolts screwed in an underside of the platform to adjustably support the platform.

9. An apparatus for testing strength of a corner portion of an object, the apparatus comprising:
    a support platform;
    an installing mechanism comprising two opposite rail plates mounted to the platform, and a slidable plate slidably mounted between the rail plates;
    a force gauge fixed to the slidable plate;
    a driving mechanism connected to the slidable plate to move the slidable plate and the force gauge;
    a clamp mechanism for clamping the object; and
    a push-pull mechanism connected to the force gauge to be pushed or pulled by the force gauge, the push-pull mechanism comprises two forcing posts to respectively abut against two sides of the object at the corner portion to exert push or pull force on the two sides of the corner portion to test strength of the corner portion;
    wherein the installing mechanism further comprises a drive block mounted to one end of the slidable plate and adjacent to the driving mechanism, the drive block defines a T-shaped through slot, the driving mechanism comprising a threaded shaft forming a guiding sleeve at an end, a flange is formed at a free end of the guiding sleeve to be received in the through slot of the drive block.

* * * * *